United States Patent [19]

Michaels

[11] Patent Number: 5,244,652
[45] Date of Patent: Sep. 14, 1993

[54] VISCOUS SURFACE ACTIVE COMPOSITION

[75] Inventor: Edwin B. Michaels, Milford, Conn.

[73] Assignee: E. B. Michaels Research Associates, Inc., Milford, Conn.

[21] Appl. No.: 673,631

[22] Filed: Mar. 22, 1991

[51] Int. Cl.⁵ .................. A61K 7/24; A61K 7/16; A61K 31/205; A61K 47/00
[52] U.S. Cl. .................................. 424/54; 424/49; 514/556; 514/774
[58] Field of Search .............. 424/54, 49; 514/556, 514/774

[56] References Cited

U.S. PATENT DOCUMENTS

| | | |
|---|---|---|
| 3,898,186 | 8/1975 | Mermelstein . |
| 4,207,198 | 6/1980 | Kenkare . |
| 4,439,355 | 3/1984 | Kenkare . |
| 4,451,385 | 5/1984 | Tavas . |
| 4,528,182 | 7/1985 | Curtis . |
| 4,554,097 | 11/1985 | Schebece et al. ............ 252/542 |
| 4,839,158 | 6/1989 | Michaels ................... 424/54 |

FOREIGN PATENT DOCUMENTS 1160485  8/1969  United Kingdom .
8704922  8/1987  World Int. Prop. O. .

OTHER PUBLICATIONS

Accepted Dental Therapeutics, American Dental Associates, Chicago, 1979, pp. 268-269.
Hart, J. R. et al., J. Soc. Cosmet, Chem. vol. 31:223-236 (Sep./Oct. 1980).

Primary Examiner—Howard T. Mars
Assistant Examiner—Rebecca Cook
Attorney, Agent, or Firm—Ladas & Parry

[57] ABSTRACT

High viscosity fluids comprising amphoteric surfactants and Type A gelatin. These compositions can be used in shampoos, dentrifices and cosmetic and pharmaceutical preparations.

11 Claims, No Drawings

VISCOUS SURFACE ACTIVE COMPOSITION

BACKGROUND OF THE INVENTION

1. Field of the Invention

The present invention relates to novel viscous surfactants compositions that liquify or become less viscous under elevated conditions of shear or temperature. In particular it relates to compositions comprising amphoteric surface active agents having a high viscosity and which produce good lather or foam. This invention also relates to a process for preparing these compositions. More particularly, the invention is concerned with compositions comprising betaines and amine oxides, Type A gelatin, non-ionic cellulose and polyhydric alcohols. These compositions can also optionally include lower aliphatic alcohols. Compositions of this invention can be used to prepare hair and body shampoos; hand cleansers; antiviral, antimicrobial or spermicidal compositions; and dentrifices.

2. Description of The Prior Art

It is known to add viscosity enhancing agents such as gums or other thickening compounds to amphoteric surfactants.

It is known that gelatin can be used in creams and hair wave set lotions to raise the viscosity of the formulation. However, gelatin forms rigid gels below 35° C., thereby making its use in personal hair care products, such as hand cleaners, hair and body shampoos difficult. At concentrations high enough to increase viscosity, gelatin forms solid gels which become non-adherent and lumpy when subjected to mechanical stress.

Useful viscosities of personal care products for efficient delivery to the hair, hands, body and teeth for cleansing purposes are generally in the range of 500 to 30,000 cps.

Usual viscosity enhancing excipients such as natural and synthetic gums when used with amphoteric surfactants can increase the viscosity of such solutions. However, when they are used to raise the viscosity much above 500 centipoises (cps) there is a marked decrease in the lathering properties of the surfactants.

U.S. Pat. No. 4,451,385 (Tavss et al.) discloses a liquid detergent composition comprising an anionic surfactant and a partially hydrolyzed protein fraction, rich in positively charged amino acids, having an isoionic point of 7 to 11 and a Bloom gel value of zero. This composition counters the irritation to the skin and eyes caused by the anionic surfactant, without decreasing the foaming and detergency properties imparted to the composition by said anionic surfactant.

U.S. Pat. No. 3,898,186 (Mermelstein et al.) discloses a mild liquid dishwashing composition containing a specified surface active system which includes an anionic surfactant; a Type B gel-forming gelatin, having a Bloom strength of 50-300 and an isoelectric point between pH 4.6 and 5.0, and an amine oxide. This composition forms a hydrophilic film on the surface of dishes when used as intended.

Type A gelatin is used in he compositions of the present invention. The compositions of the present invention form a hydrophobic film on the treated surface.

U.S. Pat. No. 4,554,097 (Schebece) discloses an elastic detergent bar type product comprising a mixture of anionic and amphoteric synthetic organic detergents, gelatin and water, that is of use as a novelty to encourage children to bathe. An amphotaric synthetic organic detergent can be triethanolammonium 1-carboxymethyl-1-carboxyethoxyethyl -2-coco-imidazoliniumbetaine. The product comprises 5–30% of gelatin, preferably Type A gelatin having a Bloom strength of 300. The product can also contain 3–20% of lower lihydric or polyhydric alcohols.

U.S. Pat. Nos. 4,207,198 and 4,439,355 (Kenkare) disclose similar elastic detergent bars of improved foaming power after use. These bars comprise a mixture of anionic detergent with amphoteric synthetic organic detergents. Amphoteric detergents that can be used are imidazolinium betaines. The composition also comprises about 8–35% of gelatin having a Bloom strength of 100–300 g and about 20–65% of a lower polyhydric alcohol.

Crocein Q, a product of Croda Inc. of New York, is a cationic quaternary derivative of hydrolyzed collagen protein and has been used as an ingredient in hair cream rinses and other compositions containing anionic and other surface active agents.

None of the above cited art discloses a gel type or high viscosity liquid composition having increased viscosity with good lathering or foaming potential. I have found that such compositions can be prepared from amphoteric surfactants, a Type A gelatin having a Bloom strength of 100–300 and a molecular weight from 75,000–300,000 and polyhydric alcohols and minor amounts of nonionic cellulose gums.

The characteristics of gels formed by gelatin alone even when diluted or prepared with gelatin of low Bloom strength, show port adherence and lack of uniformity. In contrast to the present invention, such products are not useful for a high viscosity fluid cosmetic or pharmaceutical products.

SUMMARY OF THE INVENTION

It has been found that a composition comprising an amphoteric surfactant comprising a mixture of betaines and amine oxides; Type A gelatin having a Bloom strength of 100–300 and a molecular weight from 75,000–300,000, polyhydric alcohols and nonionic cellulose gums and optionally lower aliphatic alcohols have increased viscosity and exhibit good lathering and foaming.

Accordingly, a primary object of the present invention is to provide personal care compositions, such as hand cleansers, hair and body shampoos having enhanced viscosity and good lathering or foaming properties.

Another object of the invention is to provide antiviral, antimicrobial or spermidical compositions that are less toxic to mammalian tissues or cells.

Still another object of the invention is to provide a composition that can be used in dentrifices.

Another object of this invention is to provide a process for producing these compositions.

DETAILED DESCRIPTION OF THE INVENTION

Compositions comprising a mixture of an amine oxide and betaines as amphoteric surfactants; Type A gelatin having a Bloom strength of 100–300 and a molecular weight from 75,000–300,000; polyhydric alcohols and nonionic cellulose gums and optionally lower aliphatic alcohols have increased viscosity with good lathering and foaming properties.

This invention overcomes a problem in the art, namely to increase the viscosity of personal care products without decreasing the lathering or foaming potential of the products. This invention overcomes inherent problems when gums or other thickening agents are added to amphoteric surfactants.

Other unexpected advantages of these compositions relate to skin integrity, antimicrobial activity (i.e. antibacterial, antiviral, antifungal) and oral health. These formulations are of special value for cosmetic and pharmaceutical preparations.

Amphoteric surfactants agents of use in the present invention include those of the type disclosed in U.S. Pat. No. 5,839,158, which describes mixtures of betaines and amine oxides. The betaines used in this invention are selected from the group consisting of (a) alkyl-N-betaines, alkyl-N-sulfobetaines, acyl-N-betaines, and mixtures of two or more thereof. The amine oxides used in this invention are selected from the group consisting of b) alkyl-N, N-dimethylamine oxides, alkyl-N,N-dihydroxyethylamine oxides or acylamide t-amine oxides and mixtures of two or more thereof. The term betaine when used herein means N-dimethyl glycine and its lower alkyl homologs. Unless otherwise specified an N-dimethyl compound is intended. The term sulfobetaine or sultaine means the sulfuric acid analog of such betaines.

Typically, the betaine and amine oxide components are present in a molar ratio of from 1:5 to 5:1, preferably in a molar ration of about 1:1. In general, the acid necessary to supply the required pH to the amphoteric surfactants can be any organic or inorganic acid, such as hydrochloric acid, phosphoric acid, sulfuric acid, citric acid, acetic acid or nicotinic acid. The operating pH for the surfactant composition is 4.5 to 7.0 preferably, from about 4.5 to 6.5. The pH of an aqueous solution comprising the above enumerated components is determined by employing an aqueous solution of 0.5%, by weight, total of active components typically at a glass electrode, to precisely define the acidity.

The alkyl-N-betaine, the alkyl-N-sulfobetaine and the acyl -N-betaine employed as the components (a) of the composition of the invention have structures, respectively, as follows:

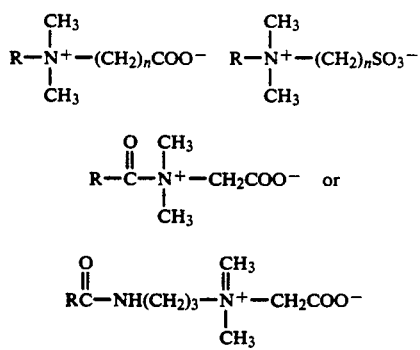

where R is a higher alkyl group having from 10 to 18 carbon atoms, preferably from 12-16 carbon atoms and where n is from 1 to 3.

Illustrative of these aforementioned substances are: (1) coco-N-betaine, cetyl-N-betaine, stearyl-N-betaine, isostearyl-N-betaine, oleyl-N-betaine; (2) coco-N-sulphobetaine, cetyl-N-sulphobetaine, stearyl-N -sulfobetaine, isostearyl-N-sulfobetaine, oleyl-N-sulfobetaine; and; (3) cocoamido-N-betaine, cetylamido-N-betaine, stearylamido-N-betaine, isostearylamido-N-betaine, oleyl-amino-N-betaine.

When used here the term "coco" is that used in the CTFA (designations of Cosmetic and Toiletry and Fragrance Association, Wash., D.C.) and is used to indicate alkyl groups present in coconut oil, i.e. a mixture of alkyl groups of from 10 to 18 carbon atoms. The designations of the compounds listed herein are those of the CTFA.

The alkyl-N,N-diethylamine oxide, (2) alkyl -N,N-dihydroxyethylamine oxide, or (3) acylamide t-amine oxide employed as component (b) of the aforementioned mixture, respectively, have the structure:

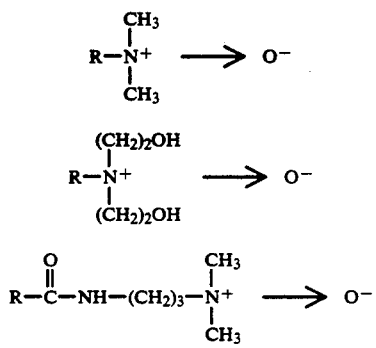

where R is a higher alkyl group of from 10 to 18 carbon atoms for instance a radical such as decyl, undecyl, lauryl, tridecyl, myristyl, cetyl, stearyl, isostearyl or oleyl. Exemplary of the amine oxides are: decyl-N,N-dimethylamine oxide, lauryl-N,N-dimethylamine oxide, stearyl-N-N-dimethylamine oxide, oleyl-N-N-dimethylamine oxide, coco-N,N dihydroxyethylamine oxide, cetyl-N-N-dihydroxyethylamine oxide, oleyl-N,N-dihydroxyethyl -amine oxide N,N-dihydroxyethlamine oxide, oleyl, N,-N-dihydroxyethyl-amine oxide and mixtures of the same. The betaine can be a alkyl-N-di(-lower alkyl) betaine preferably an alkyl N-dimethyl betaine and the amine oxide can be an alkyl-N-di (lower alkyl) amine oxide preferably an alkyl N-dimethyl amine oxide. The lower alkyl is $C_{1-3}$ Gelatin, a high molecular weight preparation of hydrolyzed collagen has inherently low viscosity under conditions where it is not forming rigid gels, is used in these compositions to form high viscosity or non-rigid gel compositions.

Gelatins such as those used in this invention are characterized by their Bloom Strength (Standard Methods for Sampling and Testing of Gelatins, Gelatin Manufacturers Institute of America, Inc., New York). Type A gelatins as used in this invention, are produced by acid processing of collagenous raw materials and have an isoelectric point between pH 7 and 9. Type B gelatins are produced by alkaline or lime processing and have an isoelectric point between pH 4.6 and 5.2. Use of Type B gelatin in compositions analogous to those of this invention inhibits the properties which are useful in this invention as the properties of the surfactants used in this invention are not compatible with Type B gelatin. In order to produce the high viscosity fluids, Type A gelatins useful in this invention will have Bloom strengths of 100 to 300. Such gelatins will have average molecular weights from about 75,000 to 3000,000.

Without wishing to be bound by any particular theories, it is generally believed that solid gel formation of gelatin is the result of hydrogen bond formation between the peptide chains of hydrolyzed collagen. These bonds are readily broken by increasing the temperature to above the melting point of the aqueous gel (usually about 35°-40° C.). The bonds reform upon cooling. It should be noted that the viscosity of gelatins are usually independent of Bloom strength, however, in the range of Bloom strength noted above (100-300), the viscosity in the compositions of this disclosure, increase with the molecular weight of the gelatin.

Illustrative of the polyhydric alcohols useful in this invention are glycerine, propylene glycol, xylitol, sorbitol, and mannitol. Cellulose gums useful in this invention are the nonionic gums such as hydroxyethyl, hydroxypropyl and hydroxypropylmethyl celluloses. The cellulose gums are those of high molecular weight. Other possible polymers are that may be used in place of the cellulose gums are, synthetic materials having some properties analogous to said gums such as polyvinyl alcohol, polyvinyl pyrrolidone and some polyacrylic acid polymer. Lower aliphatic alcohols useful in this invention are ethyl, n-propyl and isopropyl alcohols.

The compositions of this invention contain generally the following components in aqueous solution:
0.2-40% Active N Ingredient Amphoteric surfactant;
0.3-10% Type A gelatin having a Bloom strength of 100-300 and a molecular weight from 75,000 to 300,000;
0.5-30% polyhydric alcohols;
0.1-1.5% cellulose gums; and
0.0-5% lower aliphatic alcohols.

Lower chain length surfactants (e.g. coco derivatives) of the amphoteric surfactants have inherently low viscosities at useful concentrations and have the most useful foaming and lathering properties as compared to longer chain lengths.

Higher chain length derivatives (e.g. myristyl or cetyl derivatives) are useful at low concentration in oral hygiene products such as dentifrices which can benefit from having a high viscosity for dose delivery.

Typically, compositions of the present invention have a viscosity in the range 500 to 100,000 cps, preferably 1,000 to 30,000 cps. Dentrifices of this invention typically have a viscosity of 20,000-50,000 cps, preferably about 30,000 cps. When used as a dentrifice compositions of the present invention may include a polishing agent. Any such agent used however should not be one that absorbs the surfactant. Thus most silica based polishing agents should be avoided. One polishing agent that is of use is dicalcium phosphate dihydrate.

Compositions of this invention have shown particular advantages such as:

1. Gelation of the product is avoided at the ambient temperature that personal care products are normally stored and used. The viscosity remains high enough to use in the higher ambient temperatures without dripping from areas of use.

2. Synergistic effects are experienced in the combination of the mild low toxicity surfactants with the compositions above, in sharply reducing dry skin (xeroderma). This problem is serious with older people using surfactants, particularly in winter climates. This improvement is related to a moisturizing effect obtained by conserving skin hydration, which is enhanced by formulation with the above excipients.

3. These compositions can be used as topical antiinfective compositions.

In accordance with this invention, it si possible to provide high viscosity fluids which liquify under mechanical stress and at body temperature. Such products have special application in dentifrices and, in antiinfective topical agents where the high viscosity aids in dose delivery and the decrease in viscosity results in dose efficacy.

Compositions along the lines disclosed above have been used to prepare gel dentifrices which rapidly become low viscosity fluids at the mechanical stress levels and body temperatures experienced in tooth brushing. This results in enhanced therapeutic properties of dentifrices having germicidal properties, in tht the stress of brushing and the temperature in the oral cavity results in the penetration and adsorption of the therapeutic and cleansing ingredients to the subgingival sulcus and intraproximal areas of dentition.

Compositions of this invention have been used to prepare antiviral compositions for prophylactic use in treating sexually transmitted diseases. Compositions of this type are non-irritating to mammalian cells and decrease the toxicity of antimicrobial agents. These compositions can also be sued to aid wound healing.

A fuller understanding of the present invention will be gained from the following illustrative examples.

EXAMPLE 1

Amphoteric surfactants that can be used in this invention are described in Examples 1-5.

The composition described below is a concentrate of C31G, an equimolar preparation of cocobetaine and cocodimethylamine oxides (designations of CTFA Cosmetic and Toiletry and Fragrance Association, Wash., D.C.) [CFTA] which can be used in a number of different configurations. This composition is disclosed in U.S. Pat. No. 4,839,158 issued to E. B. Michaels.
Cocobetaine; 31.5% active ingredient (AI): 405.5 lb,
Cocamine oxide, 31.5% (AI); 325 lb,
Citric acid monohydrate, USP: 26 lb,
Purified water, USP: 26 lb,
To make about 782.5 lb C31G at 29.6% AI at a dilution 1% AI; pH=4.9.

EXAMPLE 2

Formulations for Contraceptive/AntiInfective Preparations

Concentrate (CCon) comprises:

| Lauryl Betaine (30% ai) | 1000 pts |
| Lauramine Oxide (30% ai) | 870 pts |
| Citric Acid monohydrate | 69 pts |

The above are stirred to a uniform solution. At a dilution of one part to 30, the composition should have a pH of 4.85 at the glass electrode. Putative concentration equal to 28.5% active ingredients (ai).

EXAMPLE 3

Cetyl betaine 20% AI: 200 lbs
Myristamine oxide 30% AI:95 lbs
Citric acid monohydrate: 6.8 lbs
Purified water:100 lbs.
To make about 402 lbs at 17% AI, at dilution 1% AI; pH 4.9.

EXAMPLE 4

Coco amido propylbetaine 30% AI:530 lbs
Cocoamido propylamine oxide 30% AI: 470 lbs
Citric acid monohydrate, USP 60 lbs Purified water, USP:100 lbs
 To make about 1160 lbs at 25.9% AI at a dilution 1% AI, pH=4.9.

EXAMPLE 5

Cocosultaine, 30% AI 347 lbs
Cocoamine oxide 30% AI 240 lbs
Citric acid monohydrate 24 lbs
Water 100 lbs
 To make about 711 lb at 24.8% AI
at a dilution 1% AI, pH=5.0.

BODY AND HAIR SHAMPOO EXAMPLES (Examples 6–13)

|  | Ex. 6 | Ex. 7 | Ex. 8 | Ex. 9 | Ex. 10 | Ex. 11[7] | Ex. 12 Prell[6] | Ex. 13 Pert Plus[6] |
|---|---|---|---|---|---|---|---|---|
| Surfactant | Ex. 1 | Ex. 1 | Ex. 1 | Ex. 1 | Ex. 1 | Ex. 2 | anionic | anionic |
| % | 7.5 | 9.0 | 9.0 | 9.0 | 9.0 | 9.0 | N/A | N/A |
| Gelatin Type | A200 | — | — | A200 | A200 | B250 | — | — |
| % | 1.0 | — | — | 1.0 | 1.0 | 1.25 | — | — |
| Hydroxy Propyl Cellulose % | 0.4 | 0.6 | — | 0.3 | — | — | — | — |
| Glycerine % | 1.0 | 1.0 | — | 0.5 | — | — | — | — |
| Excipient[1] | + | + | — | — | — | + | + | + |
| Viscosity (cps)[2] | 4400 | 800 | 80 | 3000 | 300–3000 | 1500 | 5000 | 4000 |
| Lathering hand[3] | 4.0 | 3.0 | 3.5 | 4.5 | 4.0[5] | 2.5 | 4.0 | 4.5 |
| Lathering shower[4] | 4.0 | 3.0 | 3.0 | 4.5 | — | 2.5 | 4.0 | 4.5 |

Notes
[1]The excipients are dyes and fragrances.
[2]Viscosity was measured by using a Brookfield viscometer at low stress level equivalent to pouring.
[3]Method of Hand Lathering a) clean hands b) dilute concentrate 1:5 c) rubbing hand against other hand for 60 sec. d) observe foam level at rating 0–5
[4]Method of shower lathering Foam level 0–5 based upon a volume of shampoo used. The amount of lathering produced on hair and body using a standard washing polyurethane sponge. Rating of 5 would be equivalent to use with a natural soap (Ivory liquid soap). Amount of soap used per shower would vary between 10 and 30 gms.
[5]Preparation was uneven and lumpy and was difficult to pour uniform amounts of preparation. Viscosity varied according to amount of premixing of preparation.
[6]These shampoos were used as controls. They are available commercial shampoos that have been rated by expert panels. Prell is an average foaming shampoo. Pert Plus ® is the highest foaming shampoo available on the commercial market Consumer Reports, Feb. 1989
[7]Viscosity is uneven, solution is very cloudy.

Method for Preparing Shampoos

An adequate portion of water (10X weight of cellulose gum to be used) is heated to 80° C. Cellulose gum is sprinkled into the vortex of water creating a slurry that is quickly transferred to at least 5X vol. of cold water and stirred for complete hydration by rapidly cooling to below 35° C.

Separately, gelatin should be added by sprinkling into vortex of water heated to 60° C. and stirred for short period of time to complete solution, maintaining the temperature between 40°–50° C. The gelatin solution is then transferred to the mixture of surfactants with residual water containing excipients and finally stirred with the hydrated cellulose gum to uniform solution.

Note—high speed agitation should not be used as cellulose gum will be degraded. Agitation should be strong enough as to avoid the partially hydrated cellulose gum from escaping agitation as the partially hydrated gum will have specific gravity greater than water.

DENTIFRICE EXAMPLES (Examples 14–18)

|  | Ex. 14 | Ex. 15 | Ex. 16 | Ex. 17 | Ex. 18 |
|---|---|---|---|---|---|
| Surfactant | Ex. 3 | Ex. 3 | Ex. 3 | Ex. 3 | Ex. 3 |
| % AI | 0.9 | 0.9 | 0.9 | 0.9 | 0.9 |
| Gelatin Type | A200 | A300 | A300 | A200 | — |
| % | 2.0 | 1.0 | 1.0 | 1.5 | — |
| Hydroxy Ethyl Cellulose % | 0.2 | 0.4 | 0.4 | 0.4 | 1.5 |
| Glycerine % | 11.0 | 6.0 | 6.0 | 6.0 | 2.0 |
| Alcohol | — | — | 5.0 | — | 5.0 |
| SDA 38B[1] % |  |  |  |  |  |
| Excipient[2] |  |  |  |  |  |
| Viscosity[3] | 3700/300 | 3500/1000 | 3900/1000 | 28000/100 | 52000/17000 |

[1]USP 200 proof alcohol, denatured with 1.5% mint flavor
[2]Excipients are 0.375% mint flavor N.F. 0.02% soluble saccharin U.S.P. 0.04% sodium fluoride U.S.P.
[3]Brookfield viscosity at pour stress at 70° F. over viscosity at brush stress at 95° F.

All of the gelatin gels are firm enough gels to stand up on the toothbrush. Upon delivery of the dentifrice to the dentition on brushing, the viscosity drops by about 99%, whereas with high viscosity cellulose gum (without gelatin), the dentifrice viscosity will drop less than 70% under same conditions and will be less effective. This dentifrice (without the gelatin) retains a high viscosity which inhibits the energy of tooth brushing, gum massage and diffusion of the therapeutic agent.

Preparation of Dentrifices

The flavors are stirred into the glycerine mixed with the alcohol. The gelatin and cellulose gums are triturated together and added to surfactant which is warmed to 30°–35° C. and stirred to hydrate the gum and gelatin. The saccharin and fluoride are dissolved in a small portion of water at 50° C. and are added to the hydrated solution of gums and surfactants. The glycerine and alcohol solution of the flavors are then added and the mixtures maintained at a temperature of 30°–35 ° C. The dentifrice can be packaged before the mixture has cooled below 30° C.

EXAMPLE 19

Spermicidal Gels, Cremes or Jellies for use with Cervical Caps, Condoms, Diaphragms or alone prior to coitus.

| CCon of Example 2 | 7.0 pts |
|---|---|

| | |
|---|---|
| -continued | |
| Gelatin A200 | 1.5 pts |
| Glycerine | 10.0 pts |
| Hydroxyethyl Cellulose (high viscosity Grade) | 0.4 pts |
| Water | 81.1 pts |

Procedure—The gelatin and cellulose gum are triturated in the glycerine and added to the water at 45° C. and stirred to solution. The surfactants are added to the vessel and the warm solution removed for packaging. A uniform fluid high viscosity gel forms on cooling.

EXAMPLE 20

Jelly 1 and 2

Clear fluid contraceptive jellies are prepared by substitution of 1.5 pts or high viscosity grate of hydroxypropyl or hydroxypropylmethyl cellulose for the gelatin and hydroxyethyl cellulose of the above examples.

EXAMPLE 21

Cremes 1 and 2

The Gel formulations above are converted to Creme formulations by incorporation of 0.5 pts of cetyl alcohol in Gel 1 or 2 formulations by dissolving the alcohol in the glycerine at 40° C. before trituration of the gelatin and cellulose gum.

EXAMPLE 22

Contraceptive Film 6.2 lbs of gelatin A100 is triturated with 0.5 lbs of hydroxyethylcellulose. 31 lbs of glycerine are added. Solution is mixed thoroughly to form a slurry. Add 33 lbs of CCon of Example 2 and 15 lbs of water. Warm to 40° C. Mix until gums and gelatin are completely hydrated. Solution is poured on polyethylene sheet to cast a film of abut 3 mm thick to be cut for films to be used as contraceptive films after cooling.

EXAMPLE 23

Ointment for Xeroderma 2.5 lbs of petroleum jelly is warmed to 40° C. Then mixed with 1 lb of shampoo of Example 6. Stir while cooling.

Used for moisturizing and eliminating scaly skin caused by xeroderma.

I claim:

1. A high viscosity fluid composition comprising:
  a) 0.2–40% of an aqueous amphoteric surfactant solution which comprises a mixture of a betaine selected from the group consisting of an alkyl-N-betaine, an alkyl-N-sulfobetaine and an acyl-N-betaine and mixture of two or more said betaines wherein the alkyl or acyl group contains from 10–18 carbon atoms, and an amine oxide selected from the group consisting of an alkyl-N,N -dimethylamine oxide, an alkyl-N,N-dihydroxyethylamine oxide and an acylamide t-amine oxide and a mixture of two or more said amine oxides wherein the alkyl or acyl group contains from 10–18 carbon atoms;
  b) 0.3–10% of Type A gelatin having a Bloom strength of 100–300 and a molecular weight from 75,000 to 300,000;
  c) 0.5–30% polyhydric alcohol;
  d) 0.1–1.5% nonionic cellulose gum or synthetic analog thereof; and
  e) 0.0–5% lower aliphatic alcohols.

2. The composition according to claim 1 wherein the amphoteric surfactant comprises an alkyl-N-di (methyl) betaine and an alkyl-N-di (methyl) amine oxide.

3. The composition according to claim 1 wherein the betaine is selected from the group consisting of cocobetine, lauryl betaine, cetyl betaine, and coco sultaine, and the amine oxide is selected from the group consisting of cocoamine oxide, lauramine oxide, myristamine oxide.

4. The composition according to claim 1 wherein the polyhydric alcohol is selected from the group consisting of glycerine, propylene glycol, xylitol, sorbitol and mannitol.

5. The composition according to claim 1 wherein the cellulose gum is selected from the group consisting of hydroxyethyl cellulose, hydroxypropyl cellulose and hydroxypropylmethyl cellulose.

6. The composition according to claim 1 wherein the aliphatic alcohol is selected from the group consisting of ethyl, n-propyl and isopropyl alcohol.

7. The composition according to claim 1 wherein a cellulose gum analog is selected from the group consisting of polyvinyl alcohol, polyvinyl pyrolidone and polyacrylic acid polymers.

8. The composition according to claim 1 wherein said betaine and said amine oxide are present in a ratio of from 1:5 to 5:1.

9. The composition of claim 1 further comprising petroleum jelly.

10. A method of preparing a dentrifice comprising
  a) triturating Type A gelatin having a Bloom strength of 100–300 and a molecular weight from 75,000 to 300,000 and cellulose gums together and adding to an aqueous amphoteric surfactant solution comprising a betaine selected from the group consisting of an alkyl-N-betane, an alkyl-N-sulfobetaine and an acyl-N-betaine and a mixture of two or more said betaines, and an amine oxide selected from the group consisting of an alkyl-N,N dimethylamine oxide, an alkyl-N,N-dihydroxyethylamine oxide and an acylamide t-amine oxide and a mixture of two or more said amine oxides; said gelatin being in an amount to constitute 0.3–10% of the dentrifice, said cellulose gums being in an amount to constitute 0.1–1.5% of the dentrifice and said amphoteric surfactant being in an amount to constitute 0.2–40% of the dentrifice,
  b) warming the solution of step (a) to 30°–35° C. and stirring to hydrate the gum and gelatin; and
  c) adding polyhydric alcohol in an amount to constitute 0.5–30% of the dentrifice to the solution of step (b) and maintaining the combined solution at 30°–35° C. and then cooling.

11. A method of preparing a high viscosity of fluid solution comprising: adding a nonionic cellulose gum to water in an amount to constitute 0.1–1.5% of the fluid solution,
  stirring the solution to hydrate the cellulose gum,
  preparing a separate solution of gelating by adding Type A gelatin having a Bloom strength of 100–300 and a molecular weight from 75,000 to 300,000 to water in an amount to constitute 0.3–10% of the fluid;
  transferring the gelatin solution to a mixture of an aqueous amphoteric surfactant solution, said mixture comprising a betaine selected from the group consisting of an alkyl-N-betaine, an alkyl-N-sulfobetine and an acyl-N-betaine and a mixture of two or more said betaines and an amine oxides selected from the group consisting of an alkyl-N,N dimethylamine oxide, an alkyl-N,N-dihydroxyethylamine oxide or an acylamine t-amine oxide and a mixture of two or more said amine oxides so that the amphoteric surfactant comprises 0.2–40% of the fluid, adding the solution containing gelatin and surfactants to the solution of hydrated cellulose gums, and stirring to uniform solution.

* * * * *